(12) United States Patent
Freeman et al.

(10) Patent No.: US 6,335,793 B1
(45) Date of Patent: Jan. 1, 2002

(54) PLANAR WAVEGUIDE CHEMICAL SENSOR

(75) Inventors: Neville John Freeman, Sandback; Graham Hugh Cross, Darlington, both of (GB)

(73) Assignee: Farfield Sensors Limited, Manchester (GB)

( * ) Notice: Subject to any disclaimer, the term of this patent is extended or adjusted under 35 U.S.C. 154(b) by 0 days.

(21) Appl. No.: 09/242,834

(22) PCT Filed: Nov. 19, 1997

(86) PCT No.: PCT/GB97/03093

§ 371 Date: Feb. 24, 1999

§ 102(e) Date: Feb. 24, 1999

(87) PCT Pub. No.: WO98/22807

PCT Pub. Date: May 28, 1998

(30) Foreign Application Priority Data

| Nov. 19, 1996 | (GB) | ................................. 9624010 |
| Dec. 7, 1996 | (GB) | ................................. 9625484 |
| Mar. 17, 1997 | (GB) | ................................. 9705482 |

(51) Int. Cl.$^7$ .................................................. G01B 9/02
(52) U.S. Cl. ........................................ 356/477; 356/481
(58) Field of Search ................................. 356/477, 481, 356/517; 385/12, 14; 250/227.19, 227.27, 227.14

(56) References Cited

U.S. PATENT DOCUMENTS

| 4,940,328 A | * 7/1990 | Hartman ..................... 356/481 |
| 4,950,074 A | * 8/1990 | Fabricius et al. ............ 356/481 |
| 5,262,842 A | 11/1993 | Gauglitz et al. |
| 5,377,008 A | * 12/1994 | Ridgway et al. ............. 356/481 |
| 5,825,524 A | 10/1998 | Faderl et al. |

FOREIGN PATENT DOCUMENTS

| DE | 44 19 586 A1 | 12/1995 |
| EP | 0 481 440 A2 | 10/1991 |
| EP | 0 709 710 A1 | 10/1995 |
| WO | WO 93/20430 A | 10/1993 |
| WO | WO 97/12225 | 4/1997 |

OTHER PUBLICATIONS

Chen, et al., "Electronically scanned optical–fiber Young's white–light interferometer", Optics Letters, vol. 16, No. 10, pp. 761–763, 1991.

Grattan, et al., Optical Fibre Sensor Technology, Chapman & Hall, whole document, 1995.

Borne, et al., "The Mach–zehnder interferometer; the Bates wave–front shearing interferometer", Principles of Optics—7th Edition, Cambridge University Press, pp. 348–351, 1999.

Reuter et al., Evaluating polyimides as lightguide materials, Appl. Opt., 27(21), pp. 4565–4571 (1988).

Helmers et al., Appl. Optics, 35(4). pp. 676–680, (1996).

Brandenburg et al., Integrated optical Young interferometer, Applied Optics, pp. 5941–5947, vol. 33, No. 25, Sep. 1, 1994.

Franke et al., Measuring humidity with planar polyimide light guides, Appl. Opt., 32(16), pp. 2927–2935.

Reuter et al., Monitoring humidity by polyimide lightguides, Appl. Phys. Lett. 52(10), pp. 778–779, (1988).

(List continued on next page.)

Primary Examiner—Samuel A. Turner
(74) Attorney, Agent, or Firm—Merchant & Gould P.C.

(57) ABSTRACT

A chemical sensor includes at least two wave guides, one of which is a sensing wave guide and one of which is a reference wave guide. Each of the wave guides are formed in a laminar manner on a substrate.

19 Claims, 9 Drawing Sheets

OTHER PUBLICATIONS

Podgorsek et al., Selective optical detection of n–heptane/iso–octane vapors by polyimide lightguides, Opt. Lett. 20(5), pp. 501–503, (1995).

Fabricus et al., A gas sensor based on an integrated optical Mach–Zehnder interferometer, Sensors and Actuators B, 7, pp. 672–676 (1992).

Stamm et al., Integrated optical difference interferometer as refractometer and chemical sensor, Sensors and Actuators B, 11, pp. 177–181, (1993).

Franke et al., Optical recording of refractive–index patterns in doped poly–(methyl methacrylate) films, Appl. Opt., 23(16), pp. 2729–2733, (1984).

Brandenburg et al.; Integrated optical gas sensors using organically modified silicates as sensitive films; Sensors & Actuators B11, 361–374 1993.

Heideman et al.; Performance of a highly sensitive optical waveguide Mach–Zehnder interferometer immunosensor; Sensors & Actuators B10, 209–217, 1993.

Kherrat et al, Integrated optical enlarged–field interferometer used as a chemical sensor; Sensors & Actuators B 37, 7–11, 1996.

Chen et al; A $TiO_2$ Film/$K^{30}$ Ion–Exchanged Glass Composite Optical Waveguide and Its Application to a Refractive Index Sensor; Optics Review vol. 3, 351–355, 1996.

Lukosz et al, Integrated Optical Interferometer as Relative Humidity Sensor and Differential Refractometer; Sensors & Actuators A 25–27, 185–188, 1991.

Kunz et al, Integrated Optical Sensors Based on Reactive Low–voltage Ion–plated films; Sensors & Actuators A 25–27, 155–159, 1991.

Bearzotti et al., "Integrated optic sensor for the detection of $H_2$ concentrations", Sensors and Actuators, B Chemical, vol B07, No. 1/03, Mar. 1, 1992, pp. 685–688.

N. Fabricus, "A gas sensor based on an integrated optical Mach–Zehnder interferometer", Sensors and Actuators, B. Chemical, vol. B07, No. 1/3, Mar. 1992, pp. 672–676.

* cited by examiner

PLANAR WAVEGUIDE CHEMICAL SENSOR

This invention relates to a system for sensing chemicals in order to identify chemicals present in a test material, and in order to determine the concentration of the identified chemicals in the test material.

The invention particularly relates to a system in which chemicals are sensed using the optical properties of a specialised architecture of wave guides providing either an individual chemical or physical sensor, or alternatively a number of such sensors which may be included in an array based device.

Further, the present invention relates to a system for the abstraction of data and control of interferometric chemical sensor devices.

Measuring chemical species using conventional chemical sensor technologies does not provide the level of sensitivity and robustness required and does not provide a required performance for any important applications.

Current chemical sensors incorporating transducers do not offer the sensitivity displayed, for example, by the human nose.

Known optical chemical sensors, work on the principles of interferometry.

It is known to make use of optical waveguides in which the evanescent field (that is, the field which extends outside the guiding region) is used to sense discrete changes in optical properties. This known method relies on "leakage" of optical signals from a conventional wave guide structure into a sensing layer which is typically formed from an absorbent polymer.

The evanescent component of the optical signal being guided by the wave guide is typically small leading to limited interrogation of the sensing layer.

Another disadvantage of known waveguides used as chemical sensors is that the wave guides are very sensitive to changes in temperature. As a consequence, the sensitivity of these known devices is significantly attenuated.

According to a first aspect of the present invention there is provided a sensor system having a laminate structure comprising means for providing electromagnetic radiation; two or more wave guides; propagating means for simultaneously propagating electromagnetic radiation into the two or more wave guides, each of the wave guides comprising a planar wave guide layer formed in a substrate.

In known sensors incorporating optical waveguides, a sensing layer is modified by the chemical to be tested, and evanescent excitation radiation which interrogates the sensing layer is a small fraction of the total radiation contained in the waveguide layer. As a consequence, the sensitivity of such known devices is significantly attenuated.

In contrast, the present invention incorporates a sensor in which the sensing layer is used as the wave guide for the electro-magnetic radiation, thus ensuring the majority of excitation radiation interrogates the material.

The system of the present invention therefore benefits from significant improvements in efficiency when compared to known sensors using evanescent wave strategies.

The present invention further comprises a reference wave guide in addition to a sensing wave guide, which reference wave guide is provided internally within the sensor.

The leads to a simplified structure.

The present invention provides a chemical sensor with improved reliability. The range and applicability of a chemical sensor according to the present invention is thus greatly enhanced.

The present invention provides a chemical sensor system with a novel architecture of wave guide structure which leads to a robust device with significantly enhanced signal to noise ratios (sensitivity) and discrimination.

In addition, the present invention may be used to make physical measurements relating to pressure, position or vibration or test environment or material.

The device of the present invention is suitable for detecting changes in an ambient chemical environment without being excessively stressed by other environmental factors such as temperature.

The device according to the present invention comprises an optical quantum well sensor (OQWS) which comprises two or more wave guides one of which wave guides is modified in response to chemical species present in the environment.

Preferably, the means for providing electro-magnetic radiation provides electro-magnetic radiation having a wavelength falling within the optical range.

However, it is to be understood that the invention is applicable to devices adapted for use with electro-magnetic radiation of any wavelength, for example, infra-red and ultra-violet.

Advantageously, the means for providing electro-magnetic radiation is adapted to provide plane polarised electro-magnetic radiation.

Conveniently, the system further comprises propagating means for substantially simultaneously propagating electro-magnetic radiation into the two or more wave guides.

The device may further comprise excitation means for exciting substantially simultaneously a dual or multiple symmetric wave guide system.

Preferably, the device further comprises measuring means for measuring phase changes in the electro-magnetic radiation in each of the two or more wave guides.

According to a second aspect of the present invention there is provided an apparatus comprising a plurality of sensor systems according to the first aspect of the invention, each of which devices is arranged into an array.

The sensing wave guide may be formed from silicon. Alternatively, the sensing wave guide is formed from polymeric material such as polymethyl methacrylate.

The reference wave guide may be formed from silicon oxynitride. Alternatively, the reference wave guide is formed from a polymeric material such as poly-4-vinyl pyridine P4VP. Conveniently, electrodes positioned in contact with a surface of the sensing layer enables simultaneous capacitance and optical changes to be measured as a consequence of absorption on a single device.

Conveniently, the device comprises an integrated optical device.

Conveniently, the device comprises a plurality of optical quantum well sensors.

Advantageously, the device comprises a plurality of sensing wave guide layers each of which is laid down in a laminar fashion.

Using electro-magnetic radiation of different frequencies varies the contributions of the various laminations and may further enhance the utility of the device. Preferably, both excitation modes may be used to interrogate the sensor. In other words, both the TE (transverse electric) and the TM (transverse magnetic) modes are used.

In known devices the TE mode only would be used. However, the inventors have realised that by using the TM mode as well further information may be provided.

The device according to the present invention may be a passive device, or alternatively through use of appropriate materials it may be an active optical device.

Substrates such as quartz may be used to provide an active optical device. In such a situation active feedback mechanisms may be used to compensate for temperature changes thus negating the need for a photo detector array.

The use of a plurality of wave guides leads to a highly optimised wave guide device and allows simple optical arrangements to be used.

The device according to the invention thus has fast response characteristics. The path length of each of the plurality of wave guides is long which provides greater sensitivity.

In a preferred embodiment, the wave guides are built onto a substrate through lamination processes. Such processes are highly repeatable and lead to accurate manufacture.

Due to the laminate structure of the device, the sensing wave guide and the reference wave guide are in close proximity to one another. This minimises the effects of temperature and other environmental factors.

A mixed mode device may be utilised where fundamental physical concepts such as birefringence are also used to provide additional information concerning the test chemicals.

An interference pattern is obtained when the electromagnetic radiation from both wave guide layers is coupled into free space and is recorded.

The interference pattern is used to determine the relative phase change which has occurred in the sensing wave guide with respect to the reference wave guide during the passage of electro-magnetic radiation through the structure. These are manifested as movement in the fringes and may be measured either using a single detector which measures changes in the electromagnetic radiation intensity, or an array of such devices which monitors the precise changes to the interference fringes. From the data obtained information about changes in the chemical nature of the sensing wave guide layer may be made.

The relative phase changes of the two modes are used to identify and quantify the nature of the optical changes taking place in the sensing layer. The relative phase changes of the two modes may also be used to identify such changes taking place in subsequent layers when more compact structures are employed.

The electrodes which may be laid down on the sensing layer may take the form of either parallel plates laid along side the wave guide structure or as an interdigitated or meander system laid down on the top and bottom surfaces of the sensing wave guide layer.

In the case of a meander system, the metal forming the electrode is responsible for scattering excessive amounts of light and as such the capacitance is measured on an adjacent structure which is not utilised for optical measurement. In both cases, the electrodes enable changes in capacitance of the absorbent layer to be measured.

Conveniently, measurement of capacitance and refractive mode index of the two modes yields further information on changes occurring in the absorbent layer.

The device according to the present invention may be used for making remote chemical sensor measurements and involves optical sensors of the type described hereinabove. Other technologies could also be used such as piezo-electric sensors or hot ceramic oxide devices, and condensed phase materials.

The invention can be used in a single mode of operation or in a bi-modal fashion providing additional data.

According to a third aspect of the present invention there is provided the use of a device according to the first aspect of the invention for determining chemical species.

Advantageously, there is provided a system for accurately determining chemical species, the system comprising a device according to the first aspect of the present invention further comprising:
 means for providing a purge stream; and
 means for collecting and analysing the data.

Calibration is a standard practice with laboratory based analytical equipment. Long term chemical sensing installations pose a particular problem in that detailed in situ calibrations are often inconvenient or not possible at all. As a result, the reliable performance of such devices is often impaired.

The chemical sensor system identifies chemicals of interest and is then periodically purged via a negating system using an appropriate valve system to channel the required gas streams.

The characteristics of removal of materials from the system are used to identify the analytes of interest. In using the approach, long, term drift of the sensors is compensated for, the relative response being measured rather than the absolute. In this manner, much greater sensitivity can be obtained with as long term drift of the system does not have to be accounted for when determining the limits of detection.

Typical improvements are of the region of an order of magnitude.

By measuring de-absorption aspects of the system some measure of the drift of the system can also be obtained.

The system can be run in low power mode if the power budget is limited.

An embodiment of the invention will now be further described by way of example only with reference to the accompanying drawings in which:

FIG. 5 is a schematic representation of a plate capacitor electrode arrangement suitable for forming part of a device according to the present invention;

Figure 1:
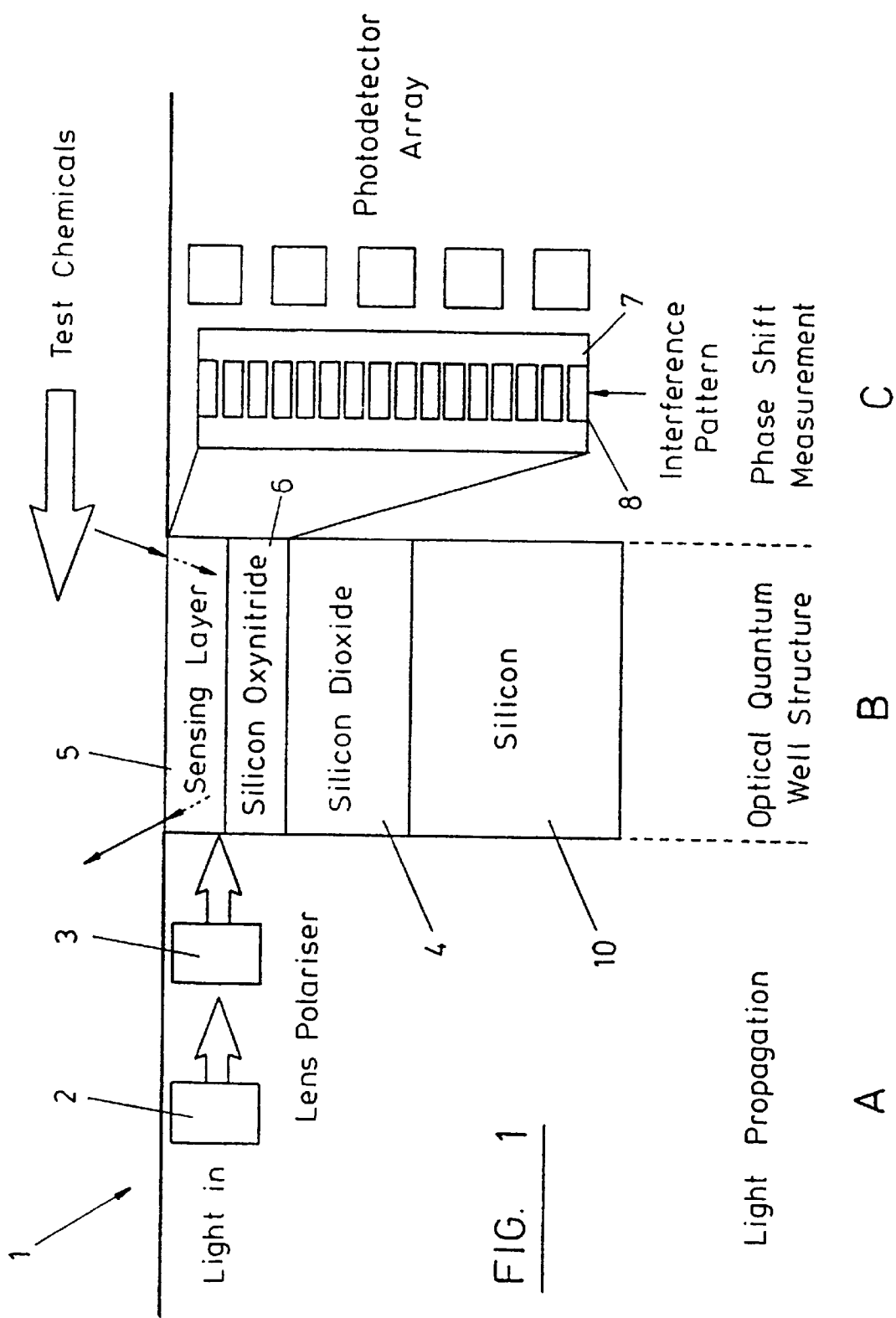
FIG. 1 is a schematic representation of an asymmetric optical quantum well sensor forming part of a device according to the present invention.

Referring to the figures a device according to the present invention is illustrated in FIG. 1 and is designated generally by the reference numeral 1.

Plane polarised optical radiation is generated from an appropriate source (not shown). The radiation is focused by lens 2 and polarised by polariser 3 directed onto the wave guide structure 4. The polariser orientates the radiation as appropriate.

Having passed through the optical wave guide 4, the radiation enters the integrated optical quantum well structure (10). The OQWS is fabricated from silicon, silicon dioxide and silicon oxynitride although other materials would also be appropriate.

The excitation radiation is passed into the sensing wave guide layer 5 and the silicon oxynitride serves as the reference layer 6 simultaneously. The OQWS has been manufactured such that the amount of radiation entering the sensing wave guide layer compared to that entering the reference layer is balanced. In other words, the amount of radiation in sensor layer 5 and reference layer 6 is approximately equal.

Having passed down the OQWS, the output radiation is coupled into free space thus generating an interference pattern depending on the test chemical passing over the sensing layer 5. The pattern is coupled to photo detector array 7 and is indicated by reference numeral 8. The pattern is used to determine the relative phase shift induced in the sensing wave guide layer when compared to the reference layer due to the presence of the test chemical passing over the sensing layer 5. The relative phase shift is directly proportional to changes occurring in the refractive index of the sensing wave guide material due to the presence of the test chemical.

The device may be placed in a chemical sampling system such that the chemicals to be tested are brought into contact with the sensing wave guide layer. As a consequence of the interaction with test chemicals by the sensing wave guide layer, changes in refractive index are effected. These changes therefore lead to changes in the relative phase shift and therefore in turn to the interference pattern which manifests itself as movement of interference fringes.

The movement of the interference fringes can be easily detected using either a single detector which records changes in the intensity of the electro-magnetic radiation incident upon it, or by using an array of detectors which monitor the change occurring in a number of fringes or the entire interference pattern.

The device illustrated in FIG. 1 may also be used to analyse a physical stimulus which may be applied to the sensing layer 5 for example via an impeller placed on the OQWS to enable the measurement of pressure or precise position, for example, to be determined.

Radiation is presented to each of the waveguides at an appropriate propagation angle which is achieved using coupling gratings or mirrors. The first may be transmissive as shown in FIG. 7, or reflective launching light down the silicon oxynitride reference wave guide.

The second is transmissive, passing light into the sensing wave guide.

The two wave guides are separated by transparent layer.

Figure 7:
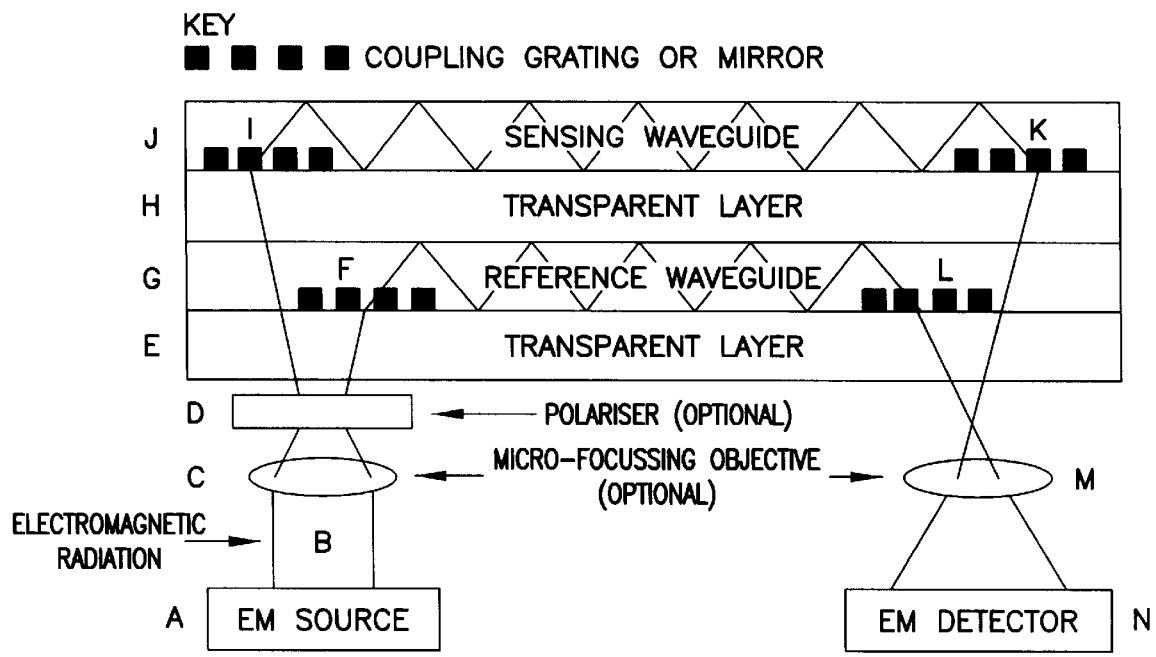
FIG. 7 is a schematic representation of a optical quantum well structure (OQWS) forming part of a device according to the present invention.

In the embodiment shown in FIG. 7, the radiation is guided out of the optical quantum well structure by further coupling gratings or mirrors. Thus, the output radiation from both wave guides is guided into free space generating interference pattern.

The output light is optionally focused using a lens or micro-focusing object.

The interference pattern is recorded by an appropriate electro-magnetic radiation detector which may comprise a single sensing element or an array of such elements.

The pattern is then used to determine the relative phase shift induced in the sensing layer when compared to the silicon oxynitride layer.

The relative phase shift is directly proportional to changes occurring in the effective refractive mode index of the sensing material.

In the system illustrated in FIG. 1, the physical and chemical stimulus to be measured comes into contact with the sensing layer. As a consequence of the physical and/or chemical changes occurring, changes in the refractive index and/or the thickness of the sensing wave guide are effected. These changes therefore lead to changes in the relative phase shift, and therefore the interference pattern which can be readily detected.

Figure 8:
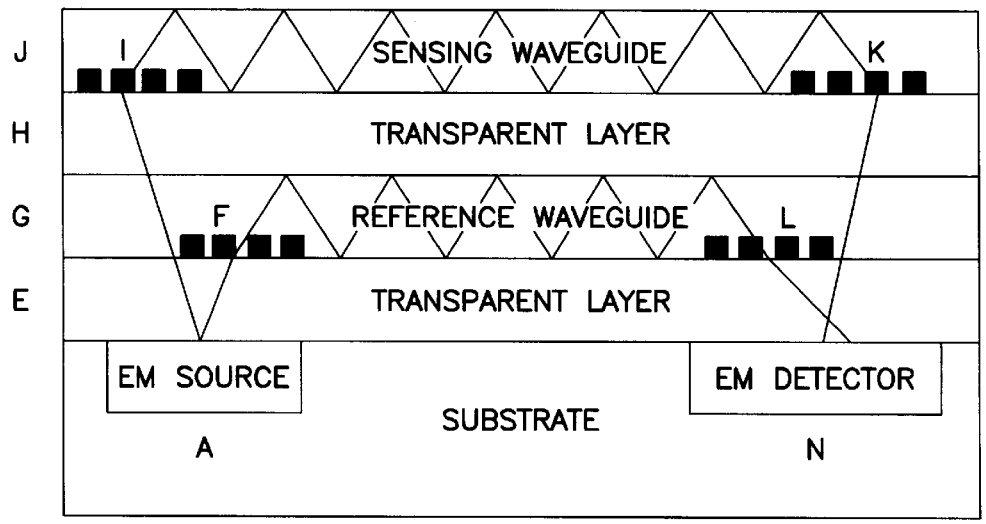
FIG. 8 is a schematic representation of an alternative OQWS.

Referring to FIG. 8, a similar structure 80 to that shown in FIG. 7 is shown but in this case the electro-magnetic radiation source and detector have been integrated onto a single structure. In this embodiment, the micro-focusing object and polariser have been omitted for clarity.

Figure 9:
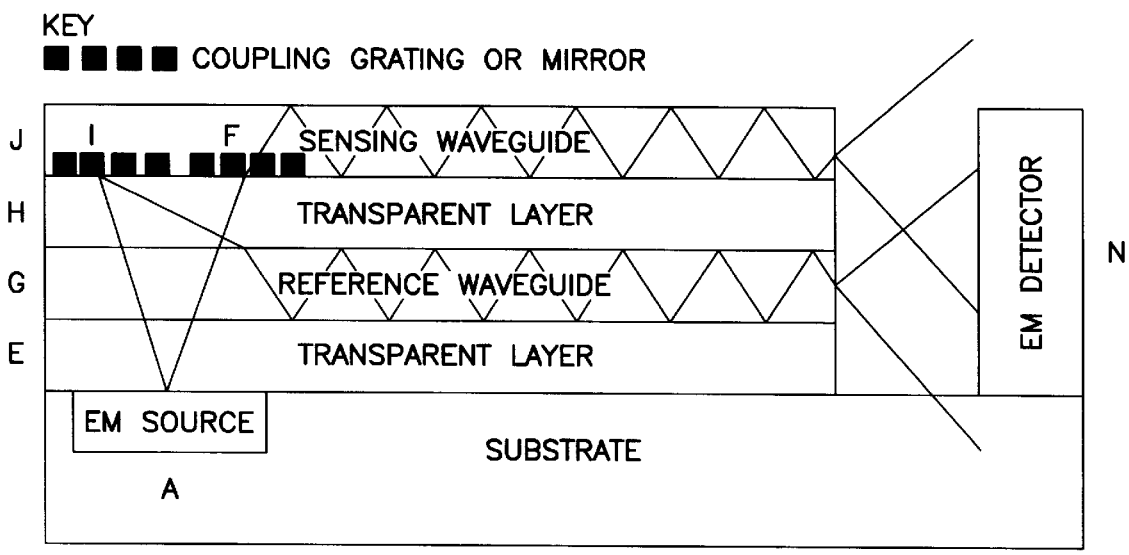
FIG. 9 is a schematic representation of yet another version OQWS.

Referring to FIG. 9 a device is shown designated generally by the reference numeral 90 in which a second pair of coupling gratings or mirrors is omitted and the output radiation is coupled into free space. The output is then monitored with an appropriate detector suitably positioned.

Figure 10:
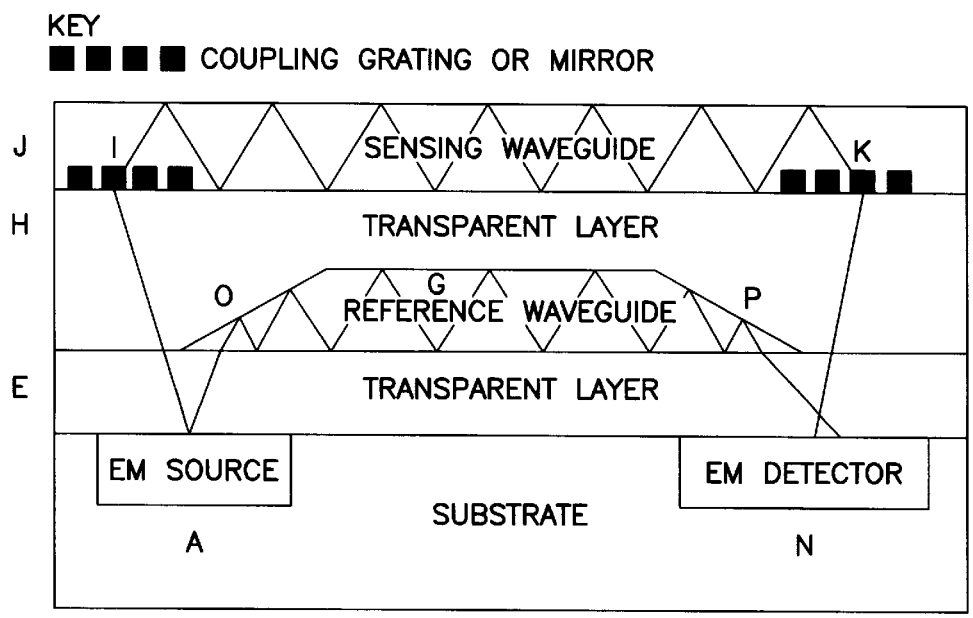
FIG. 10 is yet another embodiment of a OQWS.

A tapered end coupler rather than a coupling grating or mirror is used to propagate light into the lower reference layer as shown in FIG. 10. In this example, the light is also precisely output from the structure. However, the light may alternatively be allowed to exit the end of the structure as shown in FIG. 9.

Figure 12:
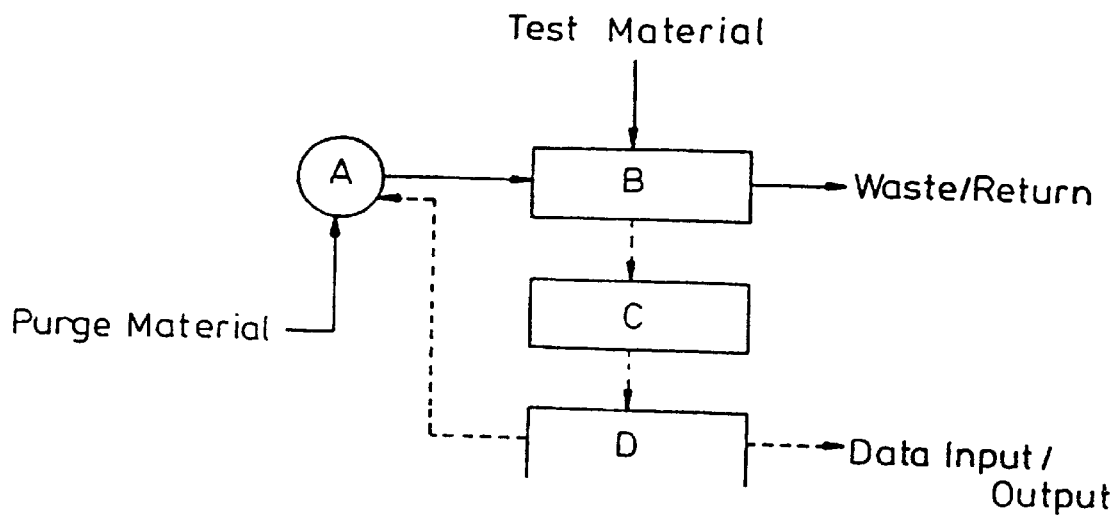
FIG. 12 is a schematic representation showing calibration of a device according to the present invention in an open instrument.

Referring to FIG. 12, a device for making remote chemical sensor measurements is shown. The instrument 120 comprises a low dead volume chemical sensor head 121, sensor electronics 122 a controller/communications function 123 and a control valve 124.

The chemical sensor system remains in contact with the test material in the case of environmental monitoring of ambient air, which may be mediated by a membrane. In this case, the transporter test material is effected passively. This is the initial mode of operation of the device.

At predefined intervals, the controller/communications function operates the control valve sweeping purge material which may in gas phase systems be nitrogen, for example, which may be obtained through pressurisation or active means such as a pump. The purge material may be provided from a central reservoir or provided locally. This perturbs the equilibrium and generates the desorption response for the chemical sensor. The characteristics of this response will be dependent upon the nature and the amounts of the chemicals in the test material. This is the second mode of operation of the device.

The advantage of the second mode of operation is that it is a relative measure and not dependent on the absolute signal of the sensor. Therefore, in principle, it is immune from any underlying drift characteristics of the system and therefore provides a much more sensitive measure of the chemical material. The purge cycle could also be used to obtain information on the underlying condition of the chemical sensor thus improving the accuracy of the initial measurement mode.

Provided that the chemical sensors are in contact with the test material, the initial measurement mode is not essential to the functioning of the invention. However, by using both sets of information a device is provided which is capable of continuous measurement with periodic measurements made with enhanced sensitivity.

Figure 13:
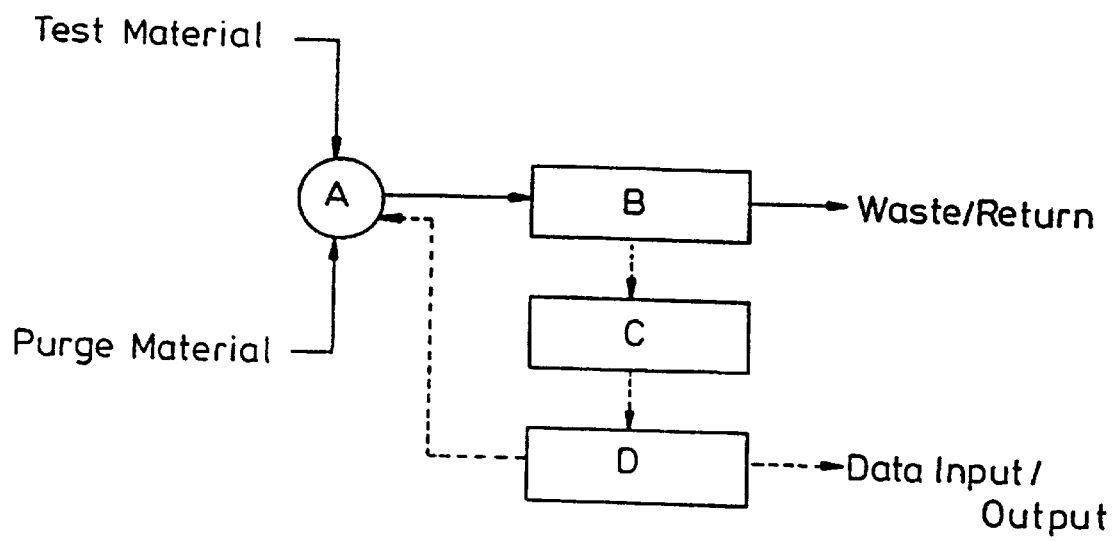
FIG. 13 is a schematic representation of a calibration of a device according to the present invention in enclosed instrument.

Referring to FIG. 13 an alternative configuration of a device according to the present invention is shown. In this case the system is closed and an active means of drawing the test material over the sensor is required in the form of a pump, for example. The closed system has some advantages over the open system as follows:
1. allowing the purging to be effected with the minimum of material which is known as purge and hold;
2. enabling purge material to reside over the chemical sensor in its rest state (where discontinuous measurements are being made).

The first feature is an advantage where extended purging times are required and/or volume of purging material is an issue. The second feature is an advantage where longevity of the chemical sensor itself is an issue.

The information provided by the devices is either logged for subsequent down load for subsequent analysis, or sent on request via a data input/output port (RF232 communications port for example).

The nature of the sensing wave guide layer is dependent upon the application to which the device is to be put.

The only requirement is that the optical properties of the material used to form the sensing wave guide layer are altered as a consequence of the desired stimulus, and that the material will transmit sufficient electro-magnetic radiation such that an interference pattern may be obtained when coupled into free space with the reference wave guide.

As such, a vast range of polymeric and other materials may be applied as a sensing layer in such devices.

One ready source of alternative materials lies in bio-materials including, but not limited to anti-bodies, enzymes and phages. Both anti-body and enzyme systems offer the potential of highly specific and highly sensitive sensors when incorporated into the sensing layer. In addition, viral and other biosystems may be employed in the sensing layer to provide critical information such as indications as to the identity of bacteria, for example.

When a detector comprises an array of sensors, the sensors may compensate for drift. Certain sensing wave guide systems will age with time, resulting in the output signal drifting. By employing an array, the drift can be monitored and a system can determine the sensor of the generated interference pattern and effectively perform the auto zero function. This is achieved by ensuring the precise region of the interference pattern which is being monitored regardless of the absolute drift in such a pattern.

The OQWS may be stimulated to produce multi-mode excitation of optical radiation. In such circumstances, by comparing the outer and inner areas of the interference pattern, it is possible to determine the extent to which the refractive index changes is induced due to changes in the thickness of the absorbent layer in its out regions and the degree to which it has been affected by physicochemical changes (in regions). The device 1 may be thermally perturbed in order to ascertain the precise degree of phase shift.

An alternative device 1 comprises a dual wave guide dual layer asymmetric system. The two wave guides 5, 6 may both be polymeric in nature and are laid down directly onto a silicon/silicon dioxide substrate. A silicon wafer with a 1 micron silicon dioxide layer is provided, upon which a 0.7 micron layer of poly-4-vinyl pyridine (P4VP) is deposited. This is analogous to the silicon oxynitride reference wave guide described hereinabove.

A subsequent layer of polymethyl methacrylate (PMMA) is laid down with a thickness of 1.5 microns to form the sensing layer.

The wafer is then diced up to provide devices of the desired dimensions which in this example are 10 mm×10 mm.

The device is then aligned using, for example, an optical stage with input from helium/neon laser using a 40× microscope objective. Alternatively, the device is coupled directly using a 5 micron optical fibre.

The optical output from the device is focused onto a pin hole photodiode or photodiode array using a 40× microscope objective, but the detector is being placed either in the near or far field.

Figure 11:
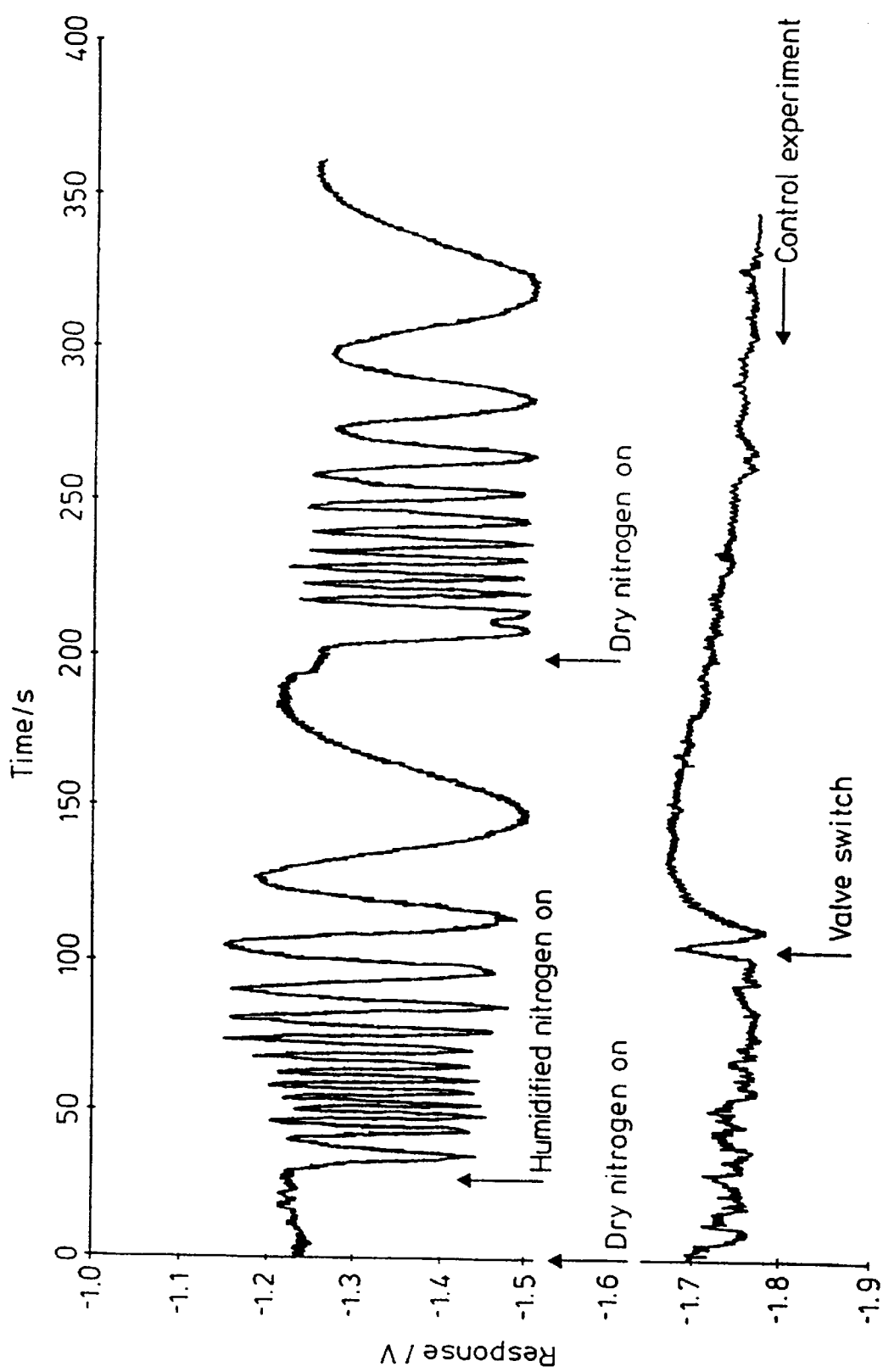
FIG. 11 is a graph showing response of an asymmetric dual wave guide sensor to humidified nitrogen.

The response of the device of FIG. 1 to water vapour as a test chemical is shown in FIG. 11.

Figure 2:
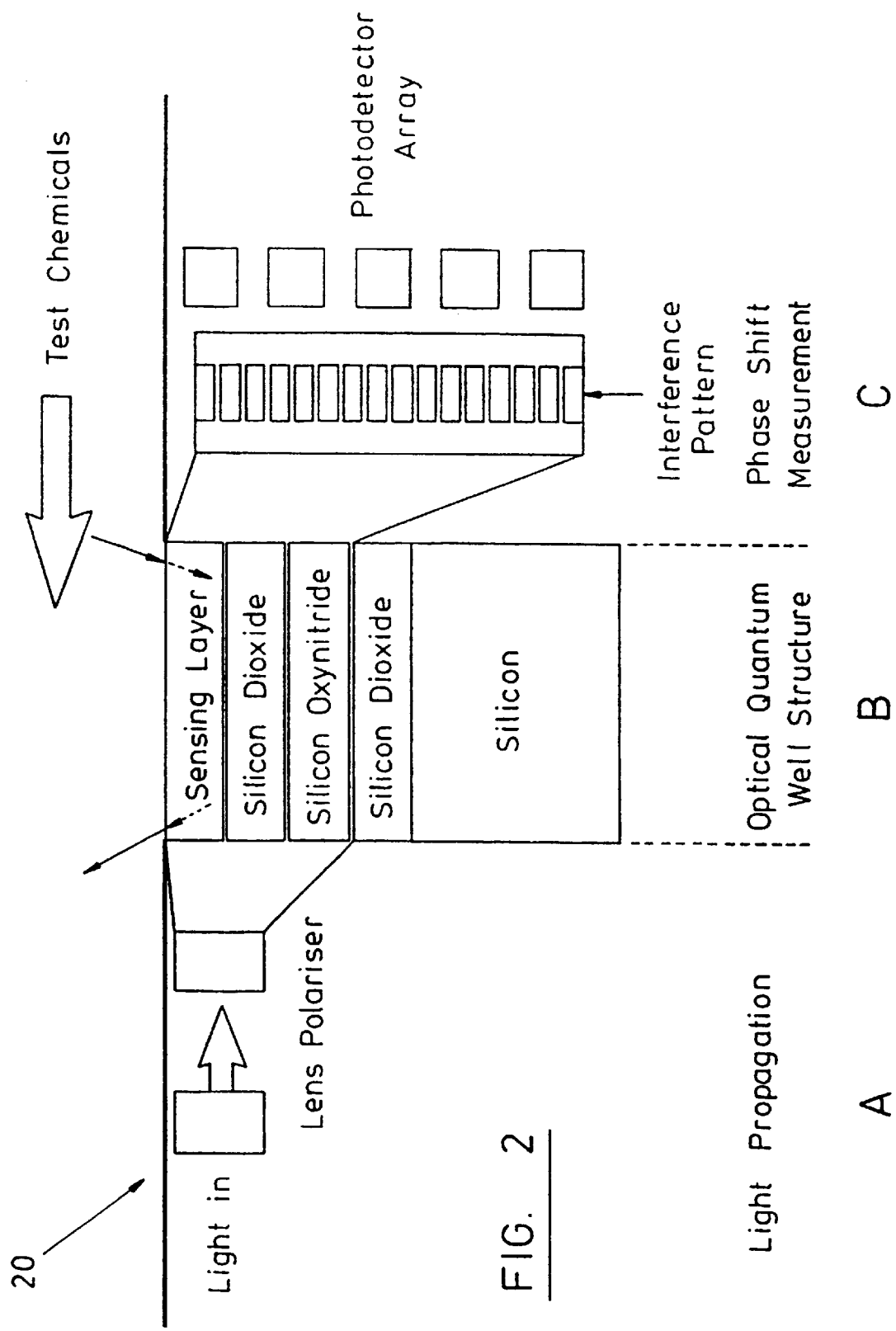
FIG. 2 is a symmetric optical quantum well sensor forming part of a second embodiment of a device according to the present invention.
Figure 3:
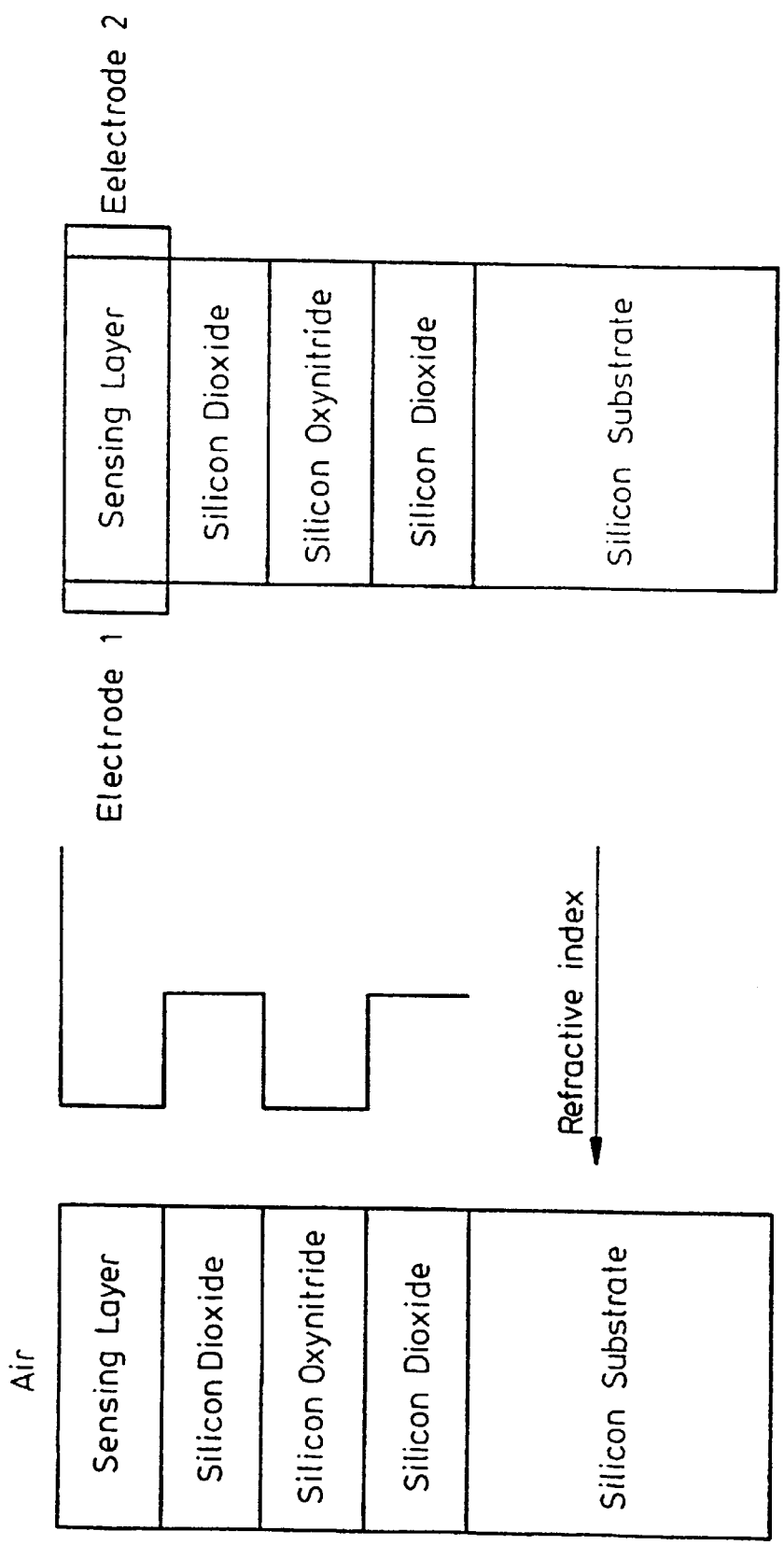
FIG. 3 is a schematic representation showing the optical characteristics of the structure of FIG. 2.
Figure 4:
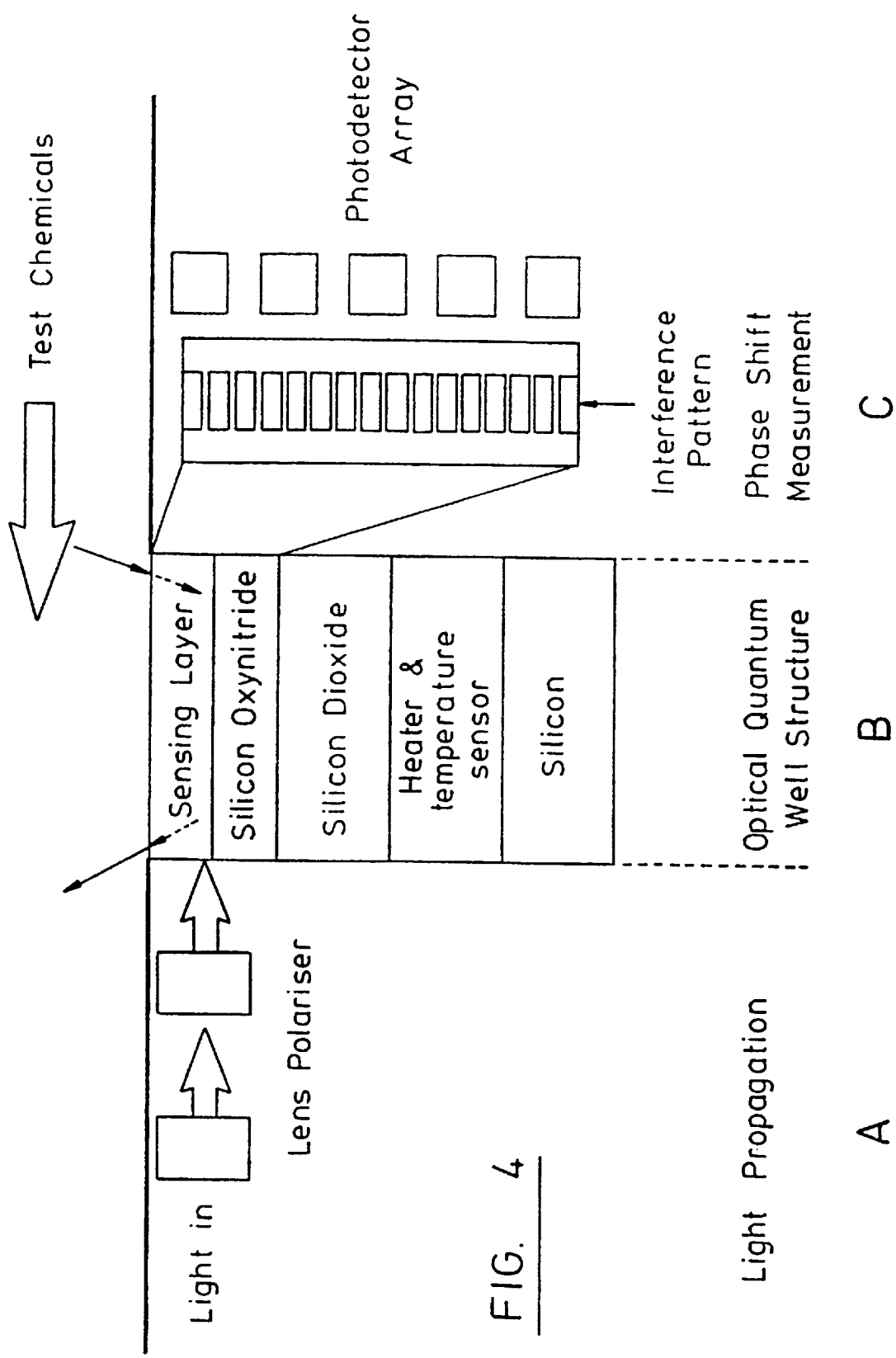
FIG. 4 is a schematic representation showing a further embodiment of the invention suitable for forming part of a thermal and multi-mode device according to an embodiment of the present invention.
Figure 6:
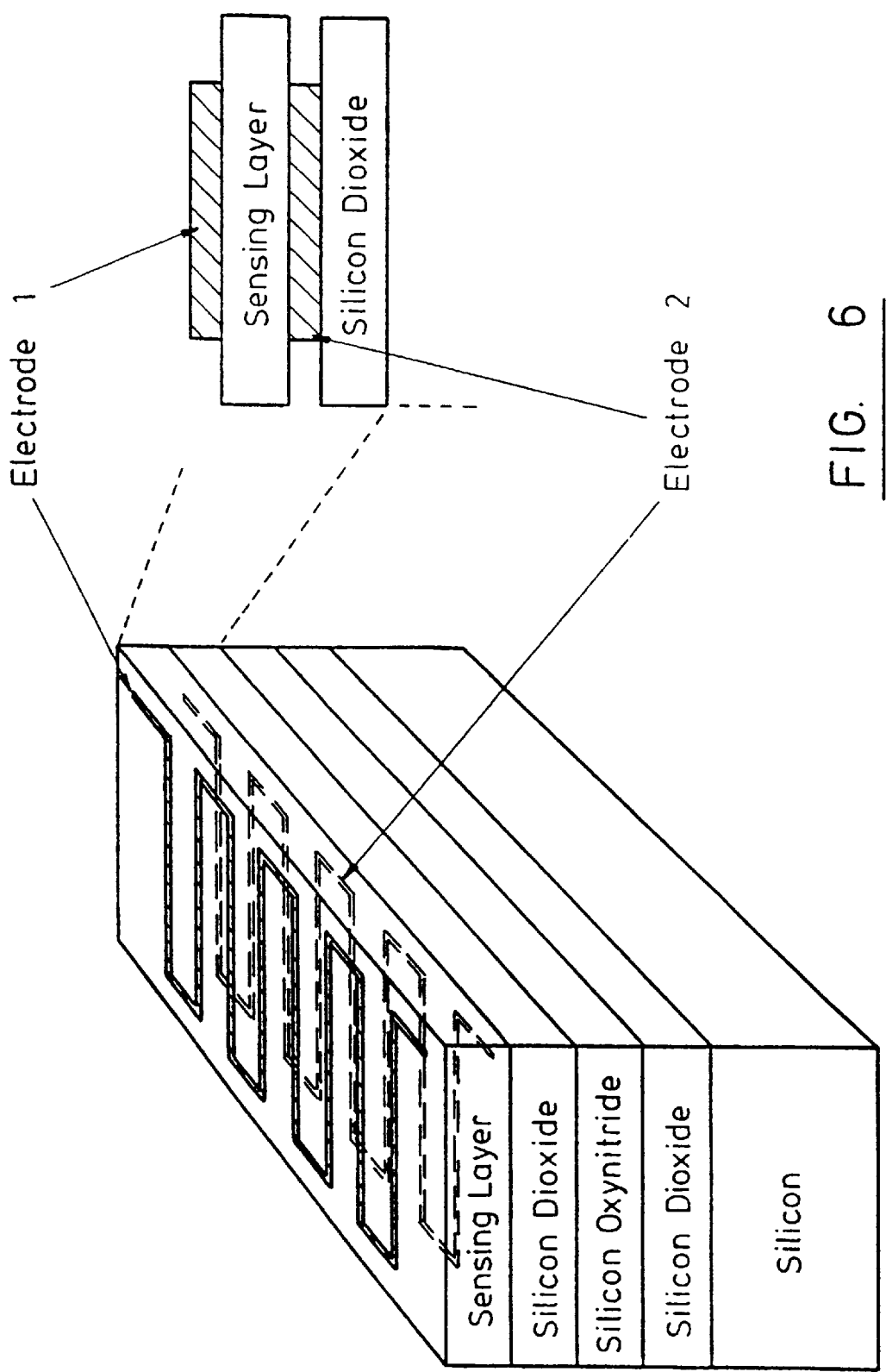
FIG. 6 is an inter-digitated electrode capacitor arrangement.

Turning now to FIG. 2, a dual wave guide, multiple layer symmetric system forming a device according to the present invention is designated generally by reference numeral 20.

A 3 micron layer of PMMA is laid down on a silicon wafer or a silicon dioxide layer. Onto this a 0.7 micron layer of P4VP is deposited forming the reference layer. A second layer of PMMA of 3.5 microns thickness is deposited to isolate the P4VP wave guide.

A second P4VP wave guide 0.7 microns thick is deposited to provide the sensing wave guide. Finally, a three micro layer of PMMA is deposited to clamp the sensing layer. A 10× microscope objective replaces the 40× objective described hereinabove with reference to FIG. 1.

What is claimed is:

1. A sensor system comprising:

a substrate;

means for providing electromagnetic radiation;

two or more waveguides having a laminate structure;

propagating means for simultaneously propagating the electromagnetic radiation into the two or more waveguides;

wherein the two or more waveguides each comprise a planar waveguide formed on the substrate.

2. A sensor system as claimed in claim 1, wherein one of the two or more waveguides is modified in response to a chemical species present in the environment.

3. A sensor system as claimed in claim 1, wherein the first waveguide is a reference waveguide and the second waveguide is a sensing waveguide.

4. A sensor system as claimed in claim 1, wherein the means for providing electromagnetic radiation provides said electromagnetic radiation having a wavelength within an optical range.

5. A sensor system as claimed in claim 1, wherein the means for providing electromagnetic radiation provides plane polarized electromagnetic radiation.

6. A sensor system as claimed in claim 1, further comprising excitation means.

7. A sensor system as claimed in claim 1, further comprising measuring means for measuring phase changes in the electromagnetic radiation in each of the two or more waveguides.

8. A sensor system as claimed in claim 3, wherein said sensing waveguide comprises silicon or a polymeric material.

9. A sensor system as claimed in claim 8, wherein said polymeric material is polymethylmethacrylate.

10. A sensor system as claimed in claim 3, wherein said reference waveguide comprises oxynitride or a polymeric material.

11. A sensor system as claimed in claim 10, wherein said polymeric material is poly-4-vinyl pyridine.

12. A sensor system as claimed in claim 3, further comprising electrodes that are laid down on the sensing waveguide.

13. A sensor system as claimed in claim 12, wherein said electrodes take the form of parallel plates laid along the two or more waveguides or interdigitated or meander systems laid down on top and bottom surfaces of the sensing waveguide layer.

14. A sensor system as claimed in claim 1 in the form of an integrated optical device.

15. A sensor system as claimed in claim 1, further comprising:

means for providing a purge system; and means for collecting and analyzing data.

16. A sensor system as claimed in claim 1, further comprising a plurality of sensing waveguide layers laid down in a laminar fashion.

17. An apparatus comprising a plurality of sensor systems as defined in claim 1, wherein each of said systems is arranged into an array.

18. A method of determining the identity of a chemical species, comprising employing the sensor system or apparatus as defined in claim 1.

19. A method for measuring physical measurements relating to pressure, position, vibration, test environment or test material, comprising employing the sensor system as defined in claim 1.

* * * * *